United States Patent [19]
Yashiki et al.

[11] 4,428,909
[45] Jan. 31, 1984

[54] ENVIRONMENTAL CONDITION SENSOR

[75] Inventors: Tomohiro Yashiki, Nara; Fumio Hosomi, Hirakata; Yasuo Wakahata, Katano; Atsushi Nishino, Neyagawa; Kiyotaka Wasa, Nara; Masazumi Katase, Katano, all of Japan

[73] Assignee: Matsushita Electric Industrial Co., Ltd., Osaka, Japan

[21] Appl. No.: 296,267

[22] PCT Filed: Dec. 24, 1980

[86] PCT No.: PCT/JP80/00323
§ 371 Date: Aug. 19, 1981
§ 102(e) Date: Aug. 19, 1981

[87] PCT Pub. No.: WO81/01880
PCT Pub. Date: Jul. 9, 1981

[30] Foreign Application Priority Data
Dec. 26, 1979 [JP] Japan .................. 54-171073

[51] Int. Cl.³ ............................................. G01N 3/16
[52] U.S. Cl. ................................. 422/95; 73/27 R; 338/22 R; 422/97; 422/98
[58] Field of Search ............................ 422/94–98, 422/90; 73/27, 23; 338/22 SD, 34, 22 R; 324/715 N; 204/195 S, 15

[56] References Cited
U.S. PATENT DOCUMENTS

| | | | |
|---|---|---|---|
| 3,159,032 | 12/1964 | Rademacher et al. | 73/359 |
| 3,522,010 | 7/1970 | Archer | 422/96 |
| 3,906,721 | 9/1975 | Micheli et al. | 60/276 |
| 4,046,645 | 9/1977 | Yoshida et al. | 204/96 |
| 4,199,425 | 4/1980 | Sinkevitch | 204/195 S |
| 4,265,724 | 5/1981 | Haecker et al. | 204/195 S |
| 4,294,801 | 10/1981 | Segawa et al. | 422/98 |

Primary Examiner—Michael S. Marcus
Attorney, Agent, or Firm—Stevens, Davis, Miller & Mosher

[57] ABSTRACT

The present invention relates to an environmental condition sensor which is used to detect temperature etc., which sensor comprises an environmental condition sensor proper (1, 3, or 7), and a gas permeable structure (2 or 5) comprising $\gamma$-$MnO_2$, (Zn—Mn—$FeO_x$), and $mAl_2O_3 \cdot nCaO$ as the main composition thereof or an enamel layer (9) comprising $\gamma$-$MnO_2$, (Zn—Mn—$FeO_x$), ($\alpha$-$Al_2O_3$·zeorite), and frit as the main composition thereof, which structure or layer surrounds the environmental condition sensor proper, so that carbon in oily smoke and uncombustion gas striking the structure burns to prevent the oily smoke and carbon from adhering to the environmental condition sensor proper (1, 3 or 7), whereby the degradation of the characteristics of the environmental condition sensor proper is avoided.

12 Claims, 3 Drawing Figures

ENVIRONMENTAL CONDITION SENSOR

TECHNICAL FIELD

The present invention relates to an environmental condition sensor which is used in conjunction with cooking equipment or a gas or petroleum heater or stove so as to detect or sense various environmental conditions such as temperatures, pressures or flow rates under which the equipment is used, thereby controlling the operation thereof.

BACKGROUND ART

Various types of environmental condition sensors have been known. For instance, temperature sensors for sensing temperatures includes thermistors, thermocouples or platinum-wire heat-responsive resistors. When these temperature sensors per se are used as temperature sensors for cooking equipment, they are exposed to smoke, unburned gases such as CO, or carbon vapor so that oil films or soot adhere to the surfaces of temperature sensors and consequently the characteristics of temperature sensors vary. Therefore, temperature sensors have previously been covered with covers such as metallic gauze or the like to prevent the adhesion of oil films or soot. However, these contaminants adhere to the cover itself so that the temperature sensor is isolated from the environmental atmosphere and consequently erratic signals are generated.

DISCLOSURE OF INVENTION

The present invention has for its object to provide an environmental condition sensor in which a sensor is surrounded with a special structure formed with one or more air holes so that smoke or carbon contained in unburned gases contacting the special structure is burned again and evaporated and consequently the adhesion of oil films or soot to the sensor proper can be avoided and the sensor can operate correctly.

BEST MODE FOR CARRYING OUT THE INVENTION

An environmental condition sensor in accordance with the present invention has an environmental condition sensor proper 1 surrounded by a structure 2 which is made of an oxidizing catalyst and has an air hole 2a.

Figure 1:
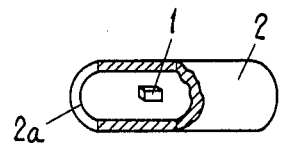
FIG. 1 is a perspective view, partly sectional, showing the basic construction of an environmental condition sensor in accordance with the present invention.

The inventors found out that when the sensor proper 1, such as a temperature sensor, is placed in a cloud of smoke produced in cooking equipment, or the atmosphere of unburned gases generated by an oil stove as shown in FIG. 1, no smoke or carbon will adhere to the sensor proper 1 and subsequent the sensor proper 1 can normally correctly operate. A possible explanation is that the structure 2, which is made of an oxidizing catalyst as shown in FIG. 1, further combusts and evaporates carbon contained in smoke or unburned gases striking the sensor proper 1.

Furthermore, the inventors found out that the structure as shown in FIG. 1 which is made of an oxidizing catalyst has an optimum composition depending upon its use. That is, the structure 2 for the sensor proper 1 which is, for instance, a temperature sensor used in cooking equipment or the like preferably has a composition such as $[(\gamma\text{-}MnO_2)+(Zn\text{-}Mn\text{-}FeO_x)+(mAl_2O_3\cdot nCaO)]$. The reason is that at a temperature range between 200° and 300° C. in the interior of cooking equipment such as gas or electric ovens the abovedescribed composition exhibits excellent properties in evaporating smoke or carbon by oxidation or decomposition thereof.

The structure can be fabricated by dry-mixing electrolytic manganese dioxide ($\gamma\text{-}MnO_2$), a composite oxide of zinc, manganese and iron ($Zn\text{-}Mn\text{-}FeO_x$) and alumina cement ($mAl_2O_3\cdot nCaO$), adding the water, sufficiently wet mixing them and pouring the mixture into a mold.

The inventors further found out the fact that a composition consisting of $[(\gamma\text{-}MnO_2)+(Zn\text{-}Mn\text{-}FeO_x)+(mAl_2O_3\cdot n\ CaO)]$ added with an extremely small amount of platinum metal is effective as the composition of the structure 2 for the sensor proper 1, such as a temperature sensor used in a petroleum or gas stove or heater. For instance, when a temperature sensor for controlling the temperature of a FF type petroleum heater is disposed according to a prior art method and exposed to the atmosphere of unburned gases for, for instance, 1,000 hours, a large amount of soot adheres to the surfaces of the environmental condition sensor so that, for instance, its electrical insulation and thermal response are degraded. However, with the structure 2 of the above-described composition, no soot adheres to the sensor proper 1 and consequently no degradation of its characteristics is observed.

The inventors further devised some techniques of fabricating the structure 2 of the above-described composition. That is, the inventors confirmed the fact that environmental condition sensors can be easily fabricated by fabricating the structure 2 by sintering the above-described composition in such a way that it surrounds the sensor proper 1; that is, with the structure 2 in the form of a cylinder. In addition, the inventors found out the fact that the structure 2 comprising a metal substrate such as aluminum or iron coated with an enamel layer composed of $[(\gamma\text{-}MnO_2)+(Zn+M+FeO_x)+(a\text{-}Al_2O_3, jeolite]$ and frit is effective in practice even if a sintered body is not used. As opposed to sintered products, metal substrates can be easily processed so that the structure 2 in any form can be easily fabricated advantageously. In this case, it is preferable that the frit used is a glass with a low softening point. Glass with a low softening point is in general lead glass. In this case, the inventors confirmed the fact that borate-silicate glass added with 1–10% by weight of, for instance, $LiO_2$ is preferable.

As described above, the present invention uses a metal substrate or base when it is coated with an enamel film or layer. However, if the sensor proper 1 is placed in the atmosphere at high temperatures higher than, for instance, 400° C., it is advantageous to use heat-resisting metal substrates or bases or heat-resisting materials such as aluminum, steatite, forsterite or zirconia.

Figure 2:
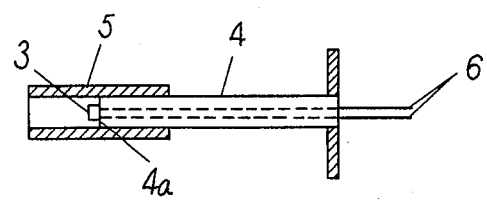
FIGS. 2 and 3 are sectional views of embodiments, respectively, of the present invention.
Figure 3:
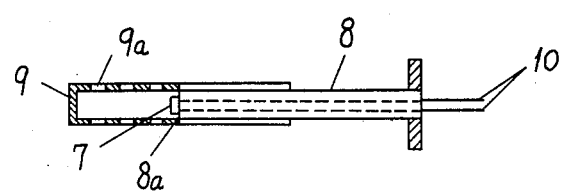

Next referring to FIGS. 2 and 3, the embodiments of the present invention will be described. The embodiments are applied to a cooking equipment. As shown in FIG. 2, a temperature sensor 3 is attached securely to one end 4a of a cylindrical holder 4 made of heat-resisting alumina and then a cylindrical sintered shape 5 of

[($\gamma$-MnO$_2$)+(Zn-Mn-FeO$_x$)+(mAl$_2$O$_3$.CaO)] is mounted so as to surround the leading end 4a of the cylindrical holder 4 and the temperature sensor 3. In this case, the temperature sensor 3 may be a thermistor, thermocouple or platinum-/wire heat-responsive resistor. 6 designates lead wires of the temperature sensor 3.

If the temperature sensor 3 is formed from a thermistor such as a silicon-carbide thermistor or a thin-silicon-film thermistor, it has a high sensitivity and exhibits a higher degree of heat-resistivity so that it is very advantageous in practice. Especially when it is used in the relatively high temperature atmosphere of 200°-300° C. (in cooking equipment), the effects of the structure 2 are remarkable.

SECOND EMBODIMENT

This embodiment is applied to a FF type petroleum heater or stove. As shown in FIG. 3, a heat-resisting, high-temperature thermistor 7 in the form of a thin silicon-carbide film is securely attached to the leading end 8a of a cylindrical holder 8 made of alumina and then a cylindrical protective tube or sheath 9 formed with air holes 9 is mounted so as to surround the thermistor 7 and the leading end 8a of the cylindrical alumina holder 8. The protective tube or sheath 9 comprises a steel or iron substrate or base plated with aluminum and further coated with enamel films or layers constituted by [($\gamma$-MnO$_2$)+(Zn-Mn-FeO$_x$)+(a-Al$_2$O$_3$, zeolite)] containing a trace of platinum metals and frit of boron-oxide-silicate glass. 10 designates lead wires of the high-temperature thermistor 7.

Although the embodiments of the present invention have been described in conjunction with temperature sensing or detection, the present invention may be equally applied effectively to other sensors sensing physical quantities such as pressures or flow rates. In addition to cooking equipment or heaters or stoves, the present invention may be equally applied to general industrial instrumentation, automotive vehicles or the like. Thus, the present invention has high industrial values.

As described above, according to the present invention, the environmental condition sensor proper is surrounded with the structure which is made of an oxydizing catalyst and has one or more air holes. As a result, the contamination of the sensor proper can be avoided and consequently variations in its characteristic can be prevented. As a consequence, reliability of the sensor proper can be improved.

INDUSTRIAL APPLICABILITY

As described previously, according to the present invention the environmental condition sensor proper is surrounded with the structure which is made of an oxidizing catalyst and has one or more air holes. Because of the function of the gas-permeable structures, carbon contained in smoke or unburned gases striking the sensor is burned and vaporizes so that no smoke or carbon will adhere to the sensor proper and consequently the degradation of characteristics of the sensor due to the attachment of smoke or carbon thereto can be avoided. The environmental condition sensors in accordance with the present invention, therefore, can be used as a sensor for sensing the temperatures of a cooking equipment, a gas heater or a petroleum heater or as a sensor used in general industrial instrumentation or automotive vehicles.

What is claimed is:

1. A temperature sensing device, comprising:
    a hollow, tubular element having an open end for gases which forms an aperture, having a composition comprising electrolytic manganese dioxide ($\gamma$-MnO$_2$), a compound oxide of zinc, manganese and iron (Zn-Mn-FeO$_x$), and alumina cement (mAl$_2$O$_3$.nCaO); and
    a temperature sensor disposed within said tubular element.

2. A temperature sensing device, comprising:
    a hollow, tubular element having a closed end and a sidewall with an aperture for gases, having a composition comprising electrolytic manganese dioxide ($\gamma$-MnO$_2$), a compound oxide of zinc, manganese and iron (Zn-Mn-FeO$_x$), and alumina cement (mAl$_2$O$_3$.nCaO); and
    a temperature sensor disposed within said tubular element.

3. A temperature sensing device as claimed in claim 1 or 2, wherein said tubular element is formed from a sintered body.

4. A temperature sensing device as claimed in claim 1 or 2, wherein said temperature sensor is spaced from said tubular element.

5. A temperature sensing device as claimed in claim 1 or 2, wherein said temperature sensor is supported on a heat-resisting support.

6. A temperature sensing device as claimed in claim 1 or 2, wherein said tubular element further comprises a trace amount of a platinum metal.

7. A temperature sensing device as claimed in claim 6, wherein said tubular element is formed from a sintered body.

8. A temperature sensing device, comprising:
    a hollow tubular element having an open end for gases which forms an aperture, comprising a substrate coated with an enamel film having a composition which comprises electrolytic manganese dioxide ($\gamma$-MnO$_2$), a compound oxide of zinc, manganese and iron (Zn-Mn-FeO$_x$), alpha alumina-zeolite ($\alpha$-Al$_2$O$_3$, zeolite and a frit; and
    a temperature sensor disposed within said tubular element.

9. A temperature sensing device, comprising:
    a hollow tubular element having a closed end and a sidewall with an aperture for gases, comprising a substrate coated with an enamel film having a composition which comprises electrolytic manganese dioxide ($\gamma$-MnO$_2$), a compound oxide of zinc, manganese and iron (Zn-Mn-FeO$_x$), alpha-alumina zeolite ($\alpha$-Al$_2$O$_3$, zeolite) and a frit; and a temperature sensor disposed within said tubular element.

10. A temperature sensing device as claimed in claim 8 or 9, wherein said substrate comprises aluminum and iron.

11. A temperature sensing device as claimed in claim 8 or 9, wherein said substrate comprises a heat resisting material selected from aluminum, steatite, forsterite and zirconia.

12. A temperature sensing device as claimed in claim 8 or 9, wherein said frit is a boron-oxide-silicate glass.

* * * * *